United States Patent [19]

Gromlich et al.

[11] 4,160,385
[45] Jul. 10, 1979

[54] PIPE QUALITY MONITORING MECHANISM

[75] Inventors: Roy J. Gromlich, Wrightstown, N.J.; Kilian H. Brech, deceased, late of New Hope, Pa., by Avis Brech, executrix; John D. Cist, Wilmington, Del.

[73] Assignees: E. I. duPont de Nemours and Co., Wilmington, Del.; Sonic Instruments, Inc., Trenton, N.J.

[21] Appl. No.: 811,975

[22] Filed: Jun. 30, 1977

[51] Int. Cl.$^2$ .................. G01N 29/04; G01B 17/02
[52] U.S. Cl. .................................................. 73/622
[58] Field of Search ........................... 73/615, 618–628

[56] References Cited

U.S. PATENT DOCUMENTS

| | | | |
|---|---|---|---|
| 2,534,006 | 12/1950 | De Lano, Jr. et al. | 73/618 X |
| 3,321,959 | 5/1967 | Wood et al. | 73/622 |
| 3,828,609 | 8/1974 | Furon et al. | 73/622 |
| 3,930,404 | 1/1976 | Ryden, Jr. | 73/622 |
| 3,961,523 | 6/1976 | Cornforth | 73/622 |
| 3,968,681 | 7/1976 | Cornforth | 73/622 |

FOREIGN PATENT DOCUMENTS

1370946 10/1974 United Kingdom ............ 73/622

*Primary Examiner*—Charles A. Ruehl
*Attorney, Agent, or Firm*—Dann, Dorfman, Herrell and Skillman

[57] ABSTRACT

As an ultrasonic transducer is continuously rotated about a pipe which is fed axially through a water-filled cavity, it sends sufficient periodic pulses to the pipe to cover essentially the entire pipe surface. The transducer also receives reflections from the outside and inside walls of the pipe from which information about pipe qualities is derived. A thickness processor module employs precision peak detectors in various circuits, including one in which flaw conditions are compared on successive rotation of the transducer in order to verify the presence of a flaw before an alarm is indicated. The thickness processor module may also provide display information about maximum and minimum values, average values, and eccentricity. In addition to the precision peak detector, there is also provided a rate of change filter which monitors rate of change of wall information and detects flaws by any major rate of change. If tolerances are exceeded in any respect or rate of change indicates a cavity or other discontinuity in the surface, alarms may be sounded, but before an alarm is sounded, verification is preferably accomplished by alarm verification, memory and logic means.

21 Claims, 15 Drawing Figures

PIPE QUALITY MONITORING MECHANISM

The present invention is directed to a pipe monitoring device and specifically to an ultrasonic device which repeatedly monitors the maximum and minimum wall thicknesses and related information to provide information which is useful in providing records and also in detecting flaws or defects in the pipe.

In the prior art, various techniques have been developed for monitoring dimensions of pipes or tubing, including some techniques which employ ultrasonics as a sensing medium. Such measurement is shown in particular in British Pat. No. 1,370,946, issued to Wavin Plastics Limited, filed May 14, 1971, and the complete specification of which was published Oct. 16, 1974. This patent discloses the use of ultrasonic pulses from a transducer to tubing transmitted through a water coupling for the purpose of sensing whether the piping is too thick or too thin. This system suggests using ultrasonic transducers at different places around the circumference of the pipe, for example, disposed at 90° with respect to each other, and even suggests that the ultrasonic generators may be arranged to reciprocate or rotate in a circumferential direction around the pipe and thereby scan the pipe. However, what is done with the pulses falls short of what is needed for a complete quality control program, particularly, where the product being inspected is polyethylene extruded pipe which is used in highly demanding applications and whose uniformity it is essential to maintain.

The present invention involves a monitoring system which is capable of doing all things that the system of the British patent can do and significantly more. In particular, this system is capable of detecting much smaller flaws or imperfections in pipe and verifying the flaw or imperfection before sounding an alarm or shutting down the system in order to avoid producing further unsatisfactory quality pipe.

The system of the present invention was developed to monitor the quality of DuPont Aldyl ® "A" pipe and tubing which are used, for example, for distribution of natural gas and have enjoyed wide acceptance in the gas industry because of its toughness, corrosion resistance, curability, ease of joining, and low cost of installation. The present system has been developed which enables an operator to visually observe the results detected by monitoring and recording instruments to record data on pipe wall thickness as related to predetermined criteria on a continuing basis. It is effective to cover all points on the entire pipe which has not been possible in the past so that there is essentially no opportunity for failure because of any point on the pipe having been overlooked. Even if the pipe is of good quality, it is important to have wall thickness gauge information for the entire length of the pipe over its entire circumference. The system of the present invention permits this kind of rigorous contemporaneous monitoring with immediate shutdown capabilities. In addition, the printout charts form a permanent record of the condition of every point on the pipe as it is manufactured which permits later study and evaluation.

In the past, a statistical approach to quality assurance using wall measurements taken at the ends of the pipe has been used and has been the best available and most reliable means of predicting dimensional variation of the pipe. However, neither such a technique nor imprecise measurement techniques can take into account, predict or discover, random defects which may occur inside the pipe, hidden from conventional means of detection. The present invention is capable of discovery of such defects and avoiding the use of such defective pipe. Of special concern are defects which cause the pipe to be thin in localized areas and subject to failure after installation.

Adding to the problems of fault location are the physical form of many faults which make them difficult to detect. A survey showed that since the inside pipe wall is cooled last, craters which form in the molded plastic tend to have a smooth rounded shape, and these craters are very difficult to detect. A goal defined in the course of the development of the present invention is detection of all defects which are one-quarter inch in diameter or larger or which thinned the wall by 10% or more.

In the course of development, various types of detection methods were considered, and in some cases tested, including capacitance, nuclear, optical, and ultrasonic techniques. As a result of the efforts made, the ultrasonic techniques were selected because the other techniques were subject to considerable error relative to the goals set. Capacitance techniques specifically involved problems because of the small dielectric constant change in the system with a small change in polyethylene pipe thickness. There were also problems foreseen about the ability to maintain adequate stable probe geometry for capacitance monitoring.

An optical approach encountered difficulty for several reasons, but primarily because of problems involved in employing a light sufficiently intense inside the pipe immediately down-stream of the extrusion die to detect the presence of spots. Such a light source was determined to be only bright enough to indicate gross defects and when made sufficiently bright, contributed enough energy to upset the pipe-quenching operation. Furthermore additives added to the pipe resin in order to improve outdoor weatherability under ultraviolet radiation run counter to the desirability of keeping the pipe translucent.

The most promising available nuclear gauge that was checked proved to be a gamma ray backscatter probe similar to the continuous wall thickness gauge mentioned earlier. Available gauges of this type measured a single point on the circumference as the pipe passed under the gauge providing an axial line measurement down the entire pipe so that use of statistical methods was still necessary to estimate thickness over the entire circumference. Other proposed nuclear gauges oscillate slowly around a portion of the pipe and back again and monitor the pipe thickness over the circumference, but gauges of this type fail to provide reliable flaw detection and are so slow in operation that they could not scan 100 percent of the pipe's surface at any rate approaching normal pipe production rates. Furthermore, their response to wall thickness change was too slow to detect a local flaw. Also, the use of the radioactive material involves some hazard and requires special precautions with the radioactive material to be used in this application. The backscatter gauge typically contained 0.010 to 0.025 Curie of radioactive material, which backscatter gauge has a time constant in the range of 0.2 second. In order to perform the job undertaken, a time constant of much less than 0.01 second was needed.

In the ultrasonic field, no commercial equipment was available for use with polymeric pipe with the required speed and accuracy. The system of the present invention developed and used for the first time with polymeric pipe uses a rotating transducer which does not oscillate to a point and then oscillate back. Rotation is possible in part because of a transformer coupling having concentric coils respectively on the rotatable and stationary parts. The beam of the transducer can be adjusted in width and, by adjusting the relationship between beam width, rotation speed and linear pipe speed, a helical inspection pattern covering all of the pipe is provided. Pipe diameters commonly used for gas, for example, can be thoroughly circumferentially inspected, thus providing a total inspection of the pipe. Ultrasonic techniques also permit a sufficiently high pulse repetition rate of the transducer to enable 100% inspection of the wall. A typical system emitting 3,000 pulses per second enables up to 3,000 individual wall thickness measurements to be made every second, for example.

The electronics provided with the ultrasonic transducer provide a large variety of monitoring possibilities as well as permanent printed records of information about wall measurements on a continuing basis. Visual displays employ digital read-out of current readings of many types of information. Visual and aural alarm equipment may be operable, for example, if the low wall threshold is not maintained. For example, typically the alarm is set to activate below a predetermined minimum wall thickness specification. Preferably, a single measurement indicating a wall thickness below or above some preset threshold is held in memory and checked on the next revolution of the transducer before the alarm circuit is activated.

In addition to a minimum and a maximum wall thickness tolerance, the present invention provides defect detection through monitoring the rate-of-change of wall thickness. Such a rate of change may indicate a weakness, such as a crater which does not necessarily drop the wall thickness below the minimum tolerance but represents a point of weakness. A wall thickness rate of change detector is employed in this circuit for detecting craters of this type on the order of a quarter of an inch or somewhat smaller. The rate of change detector will respond to rapidly decreasing wall thickness to activate an alarm circuit. Various types of alarms may respond to either the wall thinning below tolerance levels or to the location of a crater and they produce audible and general visual alarm such as a red light to alert production people and may also produce an alarm which identifies the specific location and type of problem on a control panel. The alarms may either be discontinued after a predetermined period of time or latched on once an alarm occurs, subject to manual release of the latching by an operator pushing a release button, for example.

For a better understanding of the present invention reference is made to the accompanying drawings in which.

Figure 1:
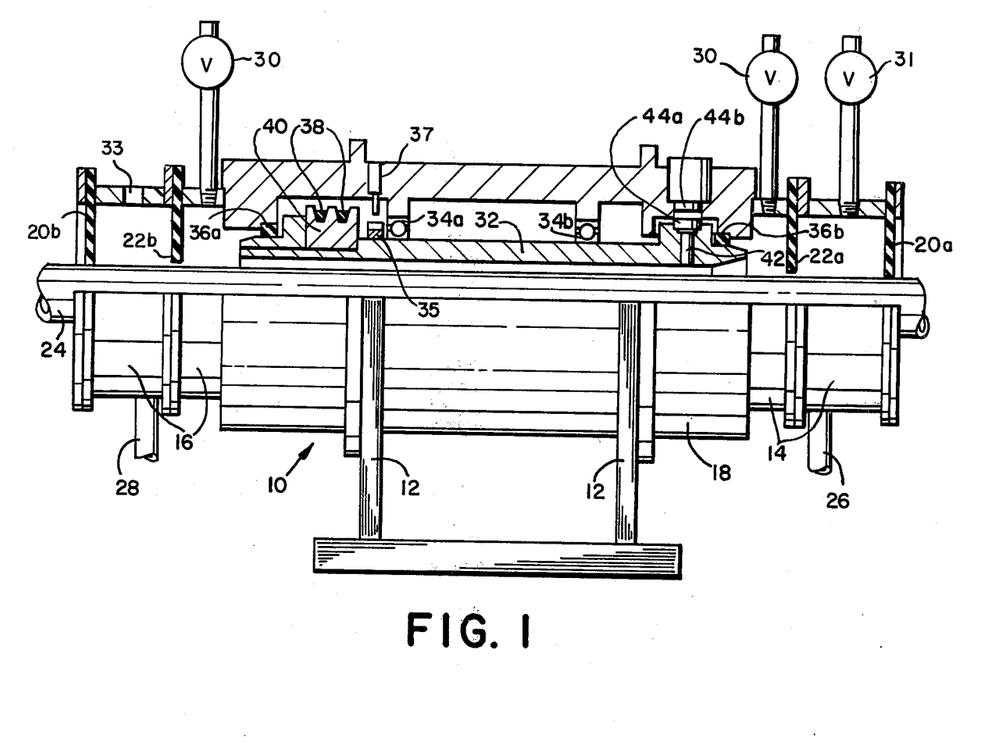
FIG. 1 is a quarter section schematic representation of the apparatus of the present invention.

Referring to FIG. 1 there is shown a tubing or pipe wall analysis equipment provided with a cylindrical housing, generally designated 10, supported on a stand 12 having smaller diameter portions 14 and 16, at the inlet and outlet ends thereof and having a larger diameter intermediate portion 18 at the midportion. End walls 20a and 20b are replaceable resilient walls of rubber or other suitable material which are provided with central openings which snugly engage and seal against the outer diameter of the cylindrical pipe 24 being fed through the apparatus 10 while similar walls 22a and 22b subdivide the smaller diameter portions 14 and 16. Walls 22a and 22b are each slightly clear of the outer diameter of pipe 24 as shown, which clearance may be about 0.001 to 0.010 inch. A water inlet 26 feeds water into the interior of the smaller diameter portion 14 between walls 20a and 22a of the cylindrical housing 10 and an outlet 28 at the opposite end removes water after it has flowed through the housing. Suitable air venting means 30 is provided to permit the escape before rotation of body 32 is started of inadvertently trapped air which rises to the top of the housing 14 and 16 as it separates from the water being introduced. The venting means 30 are each closed after rotation is started. A needle valve 31, left open continuously, vents the small diameter portion 14 between walls 22a and 20a. The small diameter portion 16 is provided with a hole 33 so that the interior of housing portion 16 between walls 22b and 22a is always at atmospheric or ambient pressure.

When the rotating body 32 is rotated, the water will be flung outward due to a centrifugal force field while gases must, of necessity, seek the "low" side of the force field, i.e., will seek the axis of rotation. Since the center portion of the apparatus is occupied by pipe, this means that gas will tend to collect at the surface of the pipe where it will be "seen" by transducer head 42 as a defect or void. The only way such entrapped gas can be removed is not by opening valves 30, but by sweeping the apparatus end-to-end by a continuous flow of water through inlet 26, through both radial clearances in walls 22a and 22b, axially along the pipe 24 and out through end portion 16 and water outlet 28.

The central enlarged portion 18 of the housing contains a generally cylindrical rotating body 32 supported by suitable bearings 34a and 34b provided with suitable seals 36a and 36b to the housing to keep water out from between the outside surface of rotating body 32 and housing portion 18. The rotating body 32 is rotatably driven by a drive belt or other suitable drive means 38 around pulley 40, said belt extending through the wall of housing portion 18 and being connected at its other end to a suitable motor or other appropriate drive to produce constant rotational speed of the rotating body 32.

Also supported on the rotational body 32 is at least one transducer head 42 connected to a winding 44a rotating with the rotating body 32 but electrically coupled to transformer winding 44b on the portion 18 of the stationary housing 10 in position from which suitable leads can be withdrawn to provide input pulses to, and to receive output pulses from, the transducer head 42. Operating clearance must be provided between the rotating body 32 and the stationary portion 18 and between the confronting faces of the windings 44a and 44b. It will be understood that an additional transducer can be, and advantageously is positioned on the rotational body 32, diametrically opposite from the transducer head 42 shown. Alternatively, multiple transducers, more than two in number, can be employed and preferably arranged at equal intervals around the periphery of the rotating body 32, preferably at the same axial cross section.

Referring to FIG. 1, in order to be able to sense the angular location of rotating body 32 it is provided with a toothed wheel 35 which is affixed to it; the wheel 35 is aligned with a fixed sensor 37 on portion 18 so that the combination produces an output pulse each time a tooth passes the sensor; the output of sensor 37 provides the tachometer output used to generate the clock pulses used in alarm verification.

Figure 2A:
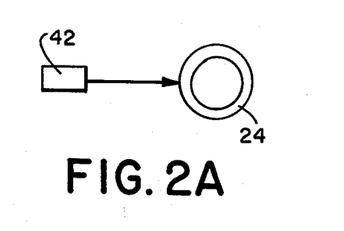
FIGS. 2A, 2B, and 2C are schematic representations of the operation of the transducer.
Figure 2B:
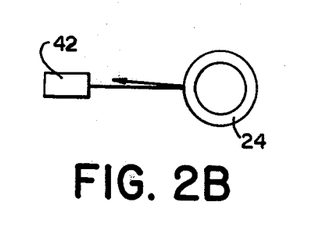
Figure 2C:
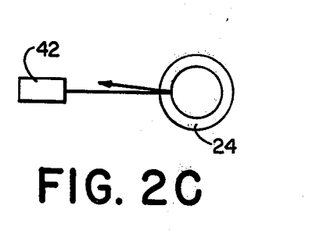

Referring now to FIGS. 2A through 2C, the operation of the transducer is diagrammed. FIG. 2A represents a pulse of sound energy being emitted by the ultrasonic transducer 42 which sound travels through the water to the outside of the pipe 24. The water provides an excellent acoustic coupling between the transducer and the pipe. FIG. 2B shows part of the sonic pulse transmitted in FIG. 2A being reflected off the outside wall of pipe 24 and back to transducer 42. The transducer receives this reflected pulse signal and transmits it to the thickness calculator. FIG. 2C shows another part of a sonic pulse reflecting off the inside wall of pipe 24 back to the transducer 42 which receives and transmits this second reflection signal to the thickness calculator. Since the time it takes each pulse to be reflected is proportional to the distance traveled, wall thickness is then calculated from the signals derived from the pulses representing the outside and the inside walls of pipe 24 at the particular point at which the pipe and the transducer are located. It will be understood that because the transducer is rotated by the rotating body 32 through belt 38 the transducer follows a circular path around the pipe 24. Therefore, successive measurements made at sixty equal intervals around the circumference will produce information on wall thickness at every 6° of rotation and the beam itself may be made sufficiently wide to cover the total 6°. It will also be understood that the pipe is moving axially through the chamber such that the speed of rotation and the linear speed of the pipe is well coordinated. The effect is to provide a helical pattern of examination of the pipe wall covering every location on the pipe wall as it passes through the chamber.

Figure 3:
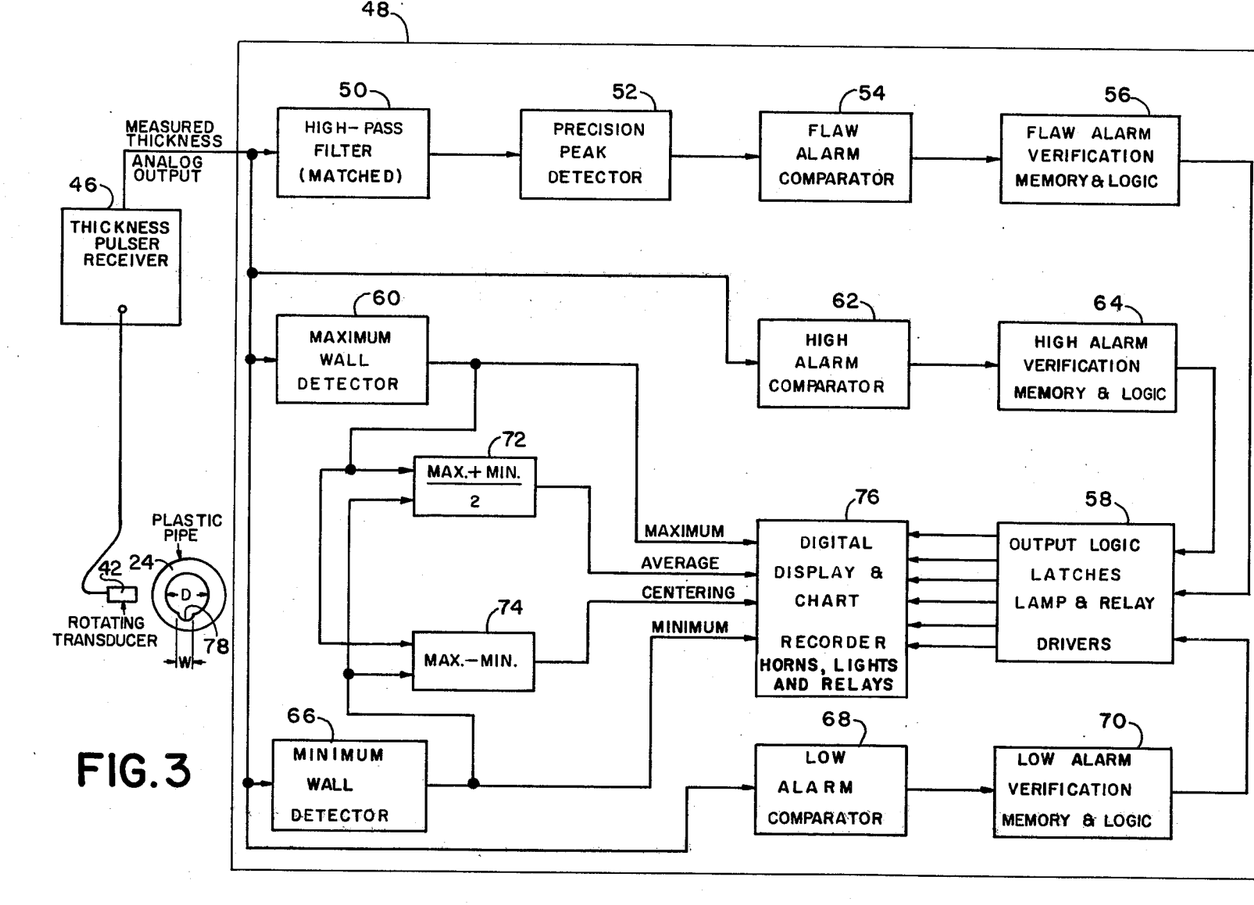
FIG. 3 is a schematic block diagram of a preferred system in accordance with the present invention.

Referring now to FIG. 3, the schematic diagram shows the process of generation of information from reflected ultrasonic pulses taken from the rotating transducer after being reflected from the resinous molded or extruded pipe, as previously described. These pulses are initiated within the thickness pulser/receiver 46 and transmitted to the transducer 42 which generates an ultrasonic pulse. The returned echoes of each ultrasonic pulse are processed by conventional electronics of the receiver which converts the time interval between received inside and outside wall pulses to analog voltage which is proportional to wall thickness.

The analog output signal is sent from receiver 46 to the thickness processor, generally designated 48, which applies the same voltage signal along several paths. The first path of the processor 48 may be a flaw detector. A second may be a high alarm. A third may be a maximum wall detector. A fourth may be a minimum wall detector. The fifth may be a low alarm detector.

Considering first the flaw alarm path, the analog voltage is applied first to a high pass filter 50, the output of which is matched to an anticipated wall thinning flaw or bubble pattern. The filtered thickness signal is fed next to a precision peak detector 52 which has the function of retaining the peak flaw amplitude for input into the flaw alarm comparator 54. The flaw alarm comparator 54 generates an output if the flaw amplitude received exceeds a selected limit. The output of the alarm comparator is applied to the flaw alarm verification memory 56 where it is stored and compared with the signal at the corresponding rotational position on the previous rotation of the transducer. The criteria are set such, for example, that, if a flaw indication occurred at the same angular position of the transducer for two successive revolutions the output logic 58 is programmed to drive appropriate indicator lights, audible devices and external control relays.

The thickness analog voltage from the thickness pulser receiver 46 is also applied to the maximum wall detector 60 which makes use of a precision peak detector, like 52, to detect and hold the largest value of wall thickness which occurs each revolution.

The thickness analog output from the thickness pulser receiver 46 is also applied to the high alarm comparator 62 where it is compared against a selected maximum value. An output is produced if the instantaneous maximum exceeds the selected limit. The output of the high alarm comparator 62 is applied to the high alarm verification memory and logic 64 where it is stored for one revolution. The verification logic compares each point in a revolution with a point at the same rotational position in the preceding revolution. An output is produced if a high limit is detected in the same rotational angular position in two successive revolutions. The output of the high alarm verification 64 is sent to the output logic system 58 where it is used to drive indicator lights, audible devices and external relays.

The analog output from the thickness pulser receiver is also applied to the minimum wall detector 66 which makes use of a precision peak detector similar to 52 in an inverted mode to detect the minimum wall thickness value in each revolution around the pipe, just as maximum wall detector 60 detects the maximum for each revolution.

The thickness analog input signal from thickness pulser receiver 46 is also applied to a low alarm comparator 68 which generates an output each time the minimum wall thickness drops below a selected limit in an opposite mode to the high alarm comparator 62. The low alarm comparator output is applied to the low alarm verification memory and logic 70 where it is stored for one revolution. The verification logic compares each point in a revolution with a point at the same position as in the preceding revolution. An output is generated whenever the low limit is detected in the same rotational angular position in two successive revolutions. The low alarm verification output is applied to output logic 58 where it is used to drive indicator lights, audible devices and external relays.

The outputs of the maximum wall detector 60 and the minimum wall detector 66 are available to drive the digital display, external recorders or data acquisition devices. Both the maximum wall and minimum wall measurements are sent to average determination circuit 72 which performs the averaging function by adding the minimum and the maximum and dividing by two. The output of the average detector is available to drive the digital display and external recorders. The maximum and minimum are also fed into the centering detector 74 which provides a measurement of eccentricity by providing the simple difference between the maximum and minimum. The output is available to drive the digital display and external recorders. The digital display and external recorders 76 in each case may operate slightly differently and it will be understood that there may be a group of these, one for each of the outputs rather than as here being a single one. They may be collected together for convenience in viewing the display.

One of the likely problems in connection with pipe being examined in accordance with the present invention is the localized thinning of the wall, usually the inside wall, which may be due to formations of bubbles or inclusions of air or gas within the resinous material forming pipe or other malformations at the exit of the forming die. This may manifest itself in a craterlike depression in the inner surface of the pipe wall. There are, of course, gradual changes of wall thickness in the normal pipe, and such changes must be distinguished. In accordance with the present invention this has been done by use of a rate-of-change filter, which detects the greater rate-of-change in the wall thickness which occurs at a bubble type flaw. The diagrammatic showing of the pipe 24 with the flaw indicated in FIG. 3 is intended to illustrate the situation. The wall thinning defects appear as rapid thickness changes, and the detector for this type of defect then must be one of several types of available circuit to recognize this rapid change. The most flexible technique is probably to use a high-pass filter to separate the rapidly changing thickness signal in a flaw and to discriminate against the lower rate-of-change of thickness in normal pipe.

Figure 4:
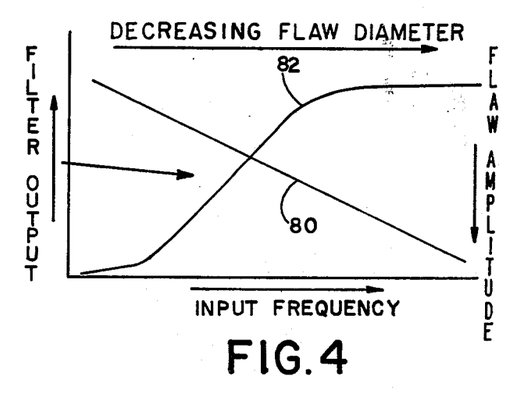
FIG. 4 is a plot with filter output amplitude versus input frequency for one type of filter.

Referring again to FIG. 3, for a given diameter of pipe, it is possible to calculate the equivalent frequency of flaws where frequency equals 1/t. "t" is the sensed defect duration in seconds and may be calculated by the following formula:

$$t = \frac{W}{\frac{RPM}{60} \pi D}$$

where D is the pipe diameter, W is the width of the flaw, both dimensions being in the same units, either inches or centimeters. Experience will tell the designer what cut-off frequencies are involved, and a corner frequency is chosen for the high-pass filter such that thickness changes having effective frequencies below the calculated flaw frequency "f" will receive higher attenuation in the filter. The equation will be understood to represent the flaw width as a segment of one revolution (N/360). Conversely, a given width of flaw "W" produces a signal whose equivalent frequency "f" is directly proportional to tube diameter. For a given diameter "D" of the pipe, the equivalent frequency "f" is inversely proportional to the size "W". FIG. 4 is intended to represent the situation applicable, that is, with a smaller flaw increasing input frequency as results with smaller craters, the amplitude of the flaw signal will decrease as shown in plot 80. However, it is possible to design a filter to have a characteristic 82 to compensate for the decreasing amplitude. This involves controlling the slope of the high-pass filter which is something that can be done within the skill of a man skilled in the filter design art.

Figure 5:
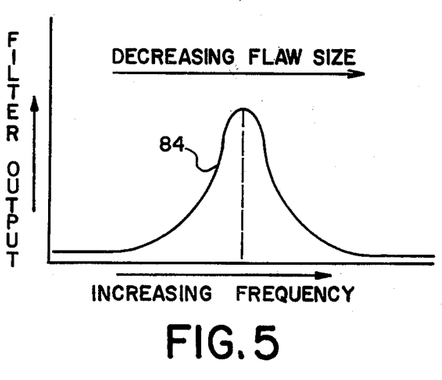
FIG. 5 is a graphical plot of another type of filter output plotted against the frequency.

Alternatively, if a high-pass filter is not desired, it is also possible to substitute a band-pass filter if the range of flaw sizes is known or to use a plurality of band-pass filters to separate different flaw sizes. FIG. 5 shows a typical band-pass filter and it will be understood that by providing a family of band-pass filters, much greater sensitivity can be achieved over different ranges of flaw size.

The output from a flaw filter is supplied to a precision negative-peak detector to detect all thinning flaws. If it is sought to detect wall thickening flaws in some other application, a positive-peak detector would be substituted. Were a full wave detector used either positive or negative changes will be detected indiscriminately.

Figure 6:
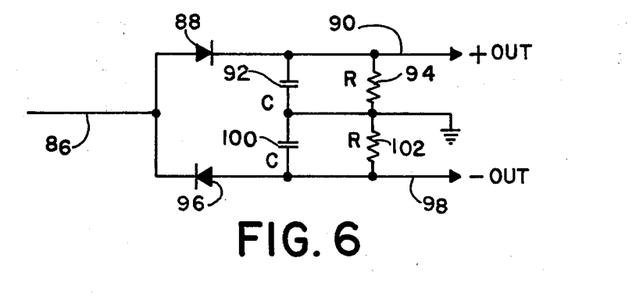
FIG. 6 is a circuit diagram of a preferred filter arrangement.

The precision peak detector is required in a number of places in the preferred system of the present invention and a simple peak detector is shown in FIG. 6. Such a peak detector circuit has a great many uses in signal processing. In many cases, such a detector operates on input signals which vary in a symmetrical way about 0 volts so that simple circuit, such as that shown in FIG. 6 is all that is needed.

Figure 7A:
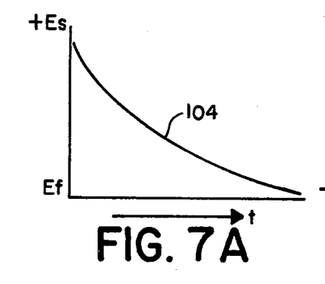
FIGS. 7A and 7B represent, respectively, outputs of the plot derived at the positive and negative terminals of the filter such as FIG. 6.
Figure 7B:
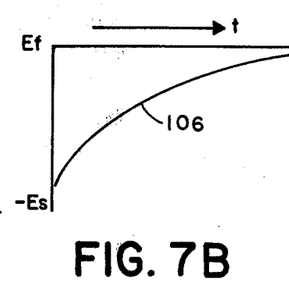
Figure 7C:
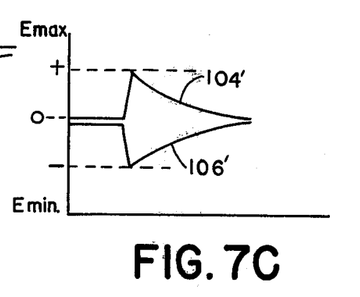
FIG. 7C represents a composite of the output of the filter of FIG. 6.
Figure 8A:
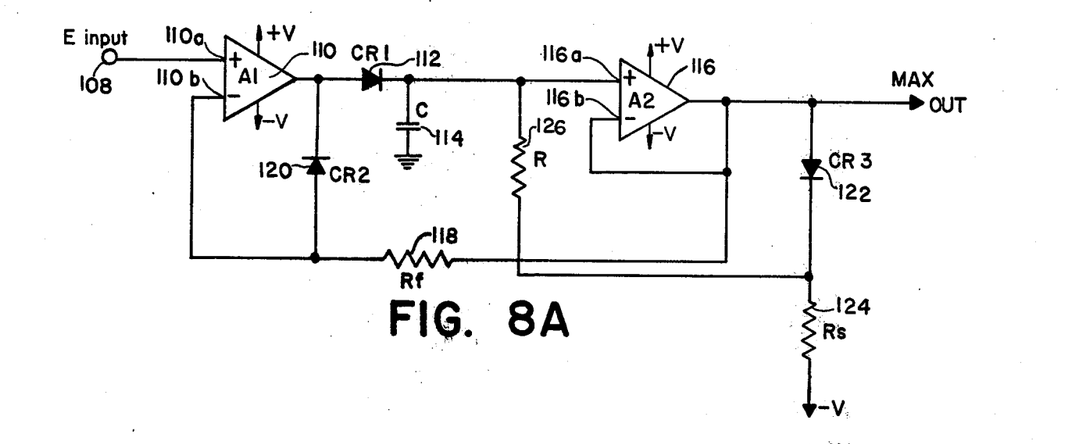
FIGS. 8A and 8B, respectively, represent maximum and minimum detectors shown as schematic circuit diagrams.
Figure 8B:
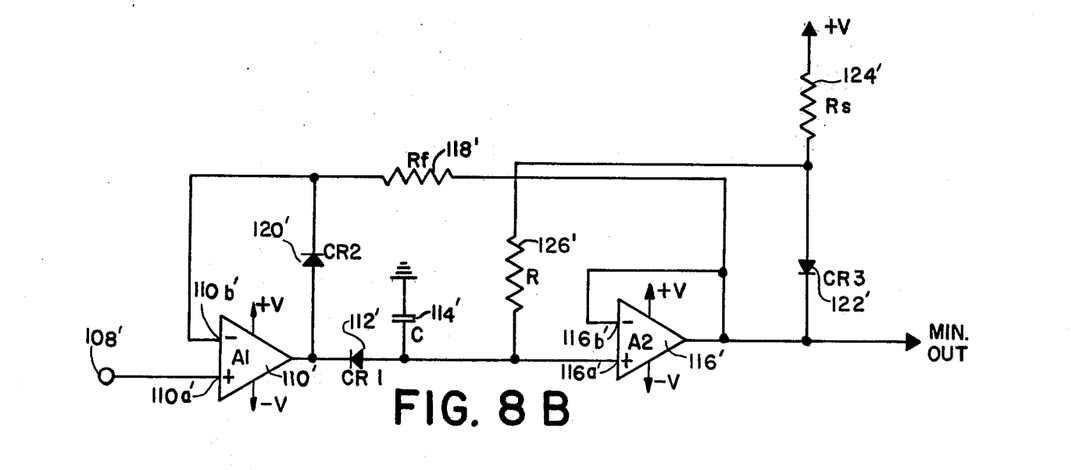

FIG. 6 shown a common input which provides a positive output through diode 88 to output terminal 90. The output is connected to ground through parallel capacitor 92 and resistor 94. Similarly, negative outputs are obtained through reversed diode 96 to negative output terminal 98 across which capacitor 100 and resistor 102 are connected in parallel to ground. Discharge current for this circuit of FIG. 6 is represented by the classical formula in which $$i = \frac{E_{start} - E_{final}}{R} \cdot e - \frac{t}{RC}$$

where i equals instantaneous current and e is the Napierian logarithm base 2.71828. FIGS. 7A and 7B show the nonlinear discharge curves which are intended to represent an exponential function by respectively decreasing with time in curve 104 or increasing in time per curve 106. In each case, the assymptotic exponential level being $E_f$. If $E_f$ has a value other than zero, the composite curve of FIG. 7C obtains for the circuit of FIG. 6 using a maximum and a minimum detector for the positive and negative signals. A complication can arise, however, if the variation is not around the average value defined by $(E_{max}+E_{min})/2=0$, such that the decay times become unequal and the curve of FIG. 7C is no longer symmetrical as shown. In either event, the maximum decays towards $E_{min}$ while the minimum decays toward the $E_{max}$ and in the unbalanced situation if the actual value is nearer to the $E_{max}$, than to $E_{min}$, the maximum detector will decay more rapidly than the minimum. To avoid this kind of problem a somewhat more sophisticated circuit is preferably provided as shown in FIGS. 8A and 8B.

The problem is eliminated by using a constant current source or sink to discharge the storage capacitor "C" in the system. If a simple semi-constant current source is used, the desired linear discharge curve will be obtained using the complementary circuits shown in FIGS. 8A and 8B. An input of E input from voltage input terminal 108 feeds terminal 110a of operational amplifier 110. This input may be the wall thickness analog from the pulser receiver or to output of the rate-of-change filter. Amplifier 110 and diodes 112 and 120 form a standard amplified diode detector. The output of diode 112 is connected ground through capacitor 114 and to terminal 116a of amplifier 116. The output of amplifier 116 is sent back through resistor 118 to terminal 110b of amplifier 110 as well as diode 120 to complete the amplified diode detector. The output is also fed back directly to terminal 116b of amplifier 116. This maximum output is also connected to power supply minus voltage supply through diode 122 and resistor 124. The output of diode 122 is fed back through resistor 126 to input terminal 116a of the amplifier 116. It will be observed that a minimum output signal is obtained from a similar circuit, corresponding parts of which are designated by the same number designators as used in FIG. 8A but with the addition of primes thereto to distinguish the parts of the respective circuits. Note that in the minimum circuit FIG. 8B the polarities of all diodes 120', 112', and 122' are reversed, as well as that of the supply voltage to RS (124').

As previously indicated, amplifier 110 and rectifiers 112 and 120 form a standard amplified diode detector whereas amplifier 116 is used as a high input impedance voltage-follower. In normal operation, feedback for amplifier 110 is obtained from the output of the amplifier 116, a low impedance point. If an input is applied to terminal 110a of amplifier 110 which is more positive than the voltage on the capacitor 114, the gain of amplifier 110 causes the diode to conduct until the voltage of the capacitance equals the E input. If E input drops below capacitor voltage $E_c$ amplifier 110 causes rectifier 112 to be reversed biased thereby isolating capacitor 114. The voltage out of voltage-follower 116 is equal to the voltage on capacitor 114 but at a low impedance. Diode 122 is connected from a low impedance of voltage-follower 116 to the negative supply via resistor 124. If that resistor 126 is chosen so that two to three milliamperes flows through rectifier 122, the voltage across rectifier 122 will be relatively constant at its intrinsic drop of about 0.63 volts.

Since amplifier 116 is a voltage-follower, the voltage at the junction of rectifier 122 and resistor 124 will always be about 0.63 volts below the voltage at capacitor 114. As the discharge resistor 126 is connected between these two points, a current constantly flows through the resistor 126, and since the two ends of resistor 126 have a constant voltage difference, the resulting current is constant.

FIG. 8B will be recognized as essentially the same circuit for the minimum output and has corresponding parts designated with the same number designators with the addition of primes.

Due to the non-ideal characteristics in the diode 122, there is some residual slope change due to the dynamic impedance of the forward biased junction. The current through the resistor 124 is not independent of the output voltage, causing some change in the diode 122 forward voltage. Additionally, temperature effects on the diode 122 drop produce changes in leakage rate. However, these effects are reduced over 100 times from the non-constant current circuit. Some small improvement in both of these characteristics is possible by using a temperature compensated Zener diode reference in place of the simple diode 122.

An alarm verification memory is included in many of the signal processing channels in order to verify that an alarm indication from the particular alarm comparator is true, for example, flaw alarm verification memory and logic 56, high alarm verification memory and logic 64, low alarm verification memory and logic 70, as shown in FIG. 3. In each case, a memory stores any alarm indications received during each revolution of the scanner around the pipe. During the succeeding revolution, the instantaneous alarm output is compared against the alarm information stored in the memory during the previous revolution. An output is produced only when the alarm indication at a particular point on the scanning rotation matches the alarm indication stored at that point in revolution during the previous scanning rotation.

In order to provide the kind of memory described, a variable length shift-register is employed. The programmable length feature of such a device allows the number of points-per-revolution to be varied as a function of the particular test configuration. Although a random access memory configuration employing either random logic or a microprocessor as the control and comparison device could be used, the simpler shift-register device is ordinarily satisfactory and, where applicable, is preferred.

In practice, each rotation of the transducer is divided into 60 parts using a 60 pulse per revolution tachometer 35. Although the choice of the 60 pulses is somewhat arbitrary, it does permit a frequency counter to give a reading directly in rotations per minute as a matter of convenience. Any other number could be used by changing the tachometer and shift-register length. For practical sizes of pipes manufactured to date, the resulting 6 degree increments cover a sufficiently small area of the pipe surface to give required coverage and at the same time provide sufficient resolution.

Figure 9:
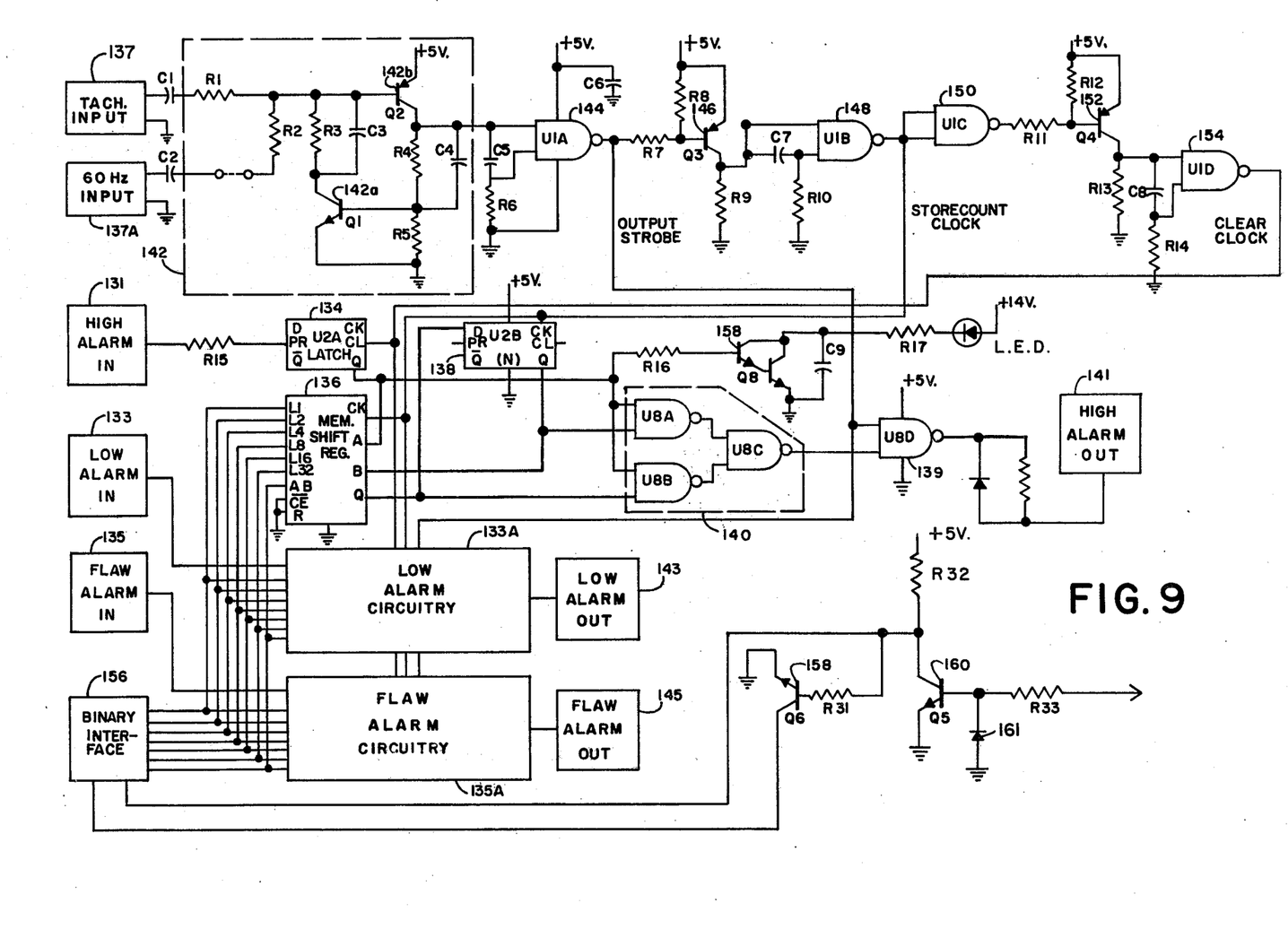
FIG. 9 represents a schematic circuit diagram of the detector circuits of the present invention in one preferred embodiment.

In operation, the latch 134 stores information received, including information which would constitute a flaw occurring within each 6 degree segment. During the next 6 degree segment, the stored value is placed into the shift-register 136 and compared with the value stored in that location for the corresponding one in the previous revolution. If both values indicate a flaw, an output is produced by the logical comparator 140.

The direct alarm information is also compared with the memory location immediately preceding its location in the last revolution. This affords a double check in case an error might have occurred and eliminates the possibility that such things as jitter in the drive speed or clock generator could cause an alarm to be missed.

By comparing each alarm indication against the same point in the previous scan, electrically induced false alarms and those caused by gas bubbles can be discriminated against and distinguished from other defects previously described, since such false alarms are unlikely to appear synchronously with the scanner rotation. It is to be observed that verification of this sort can be employed with a system in which the pipe is rotating and the sensor is fixed. In such a system, however, a clock generator or tachometer driven from the rotating part would be necessary to keep the effects of any slippage in rotation to minimum. In other respects, the system would be essentially the same.

FIG. 9 is a schematic circuit diagram of alarm verification circuitry. Inputs coming from prior circuitry generating high alarm signals 131, low alarm signals 133, and flaw alarm signals 135 are applied to similar circuit elements. On a real time basis the input for the high alarm is typical and is fed first from the high alarm comparator to the input synchronizing latch, flip-flop 134. A negative going alarm pulse at the preset input of synchronizing latch 134 causes its Q output to go high and it will remain in this state until a negative going clear clock pulse edge is received at its clear input, at which time its Q output goes low. In the connection, reference is made to the time related diagrams of FIG. 10 wherein it is shown that a tachometer output wave a can be converted to a square wave b by conventional techniques and each positive-going step of the square wave can be used to generate a clock pulse c by a Schmitt trigger, or the like. A high signal d is of the type shown in FIG. 10 marked "flaw". Similar signals and events occur in the low 133a and flaw 135a verification systems. The chart is intended to show the recurring nature of such a signal so that coincidence on repetitive cycles of rotation as shown will confirm the flaw and generate an output perhaps in the form of a pulse as shown in the decoder trace i.

When a Q output from input latch 134 is caused to go high, it remains in this state until a negative-going clear clock pulse edge is received at its clear input, at which time that Q output goes low. The Q outputs of the input synchronizing latches, such as 134, are applied to the A input of the memory shift-registers, here memory shift-register 136 for the high alarm system.

The memory shift-register 136 delays the output pulses from input latch 134 by a preset number of clock pulses e. For example, it would delay it 59 counts per revolution for a single transducer or 29 counts for a two transducer situation. At the end of the preset number of clock pulses e, the pulse from latch 134 arrives at the Q output of the memory shift-register 136. The delay length of the memory shift-register in every case is automatically programmed for use with one or two pulser/receivers 46, according to the use of one or two transducers. A 60 count (or a 30 count) signal from the unused channel shutdown section (not shown) causes the program transistors 158 and 160 to encode the binary encodeable interface 156 to select the proper memory shift-register length. Diode 161 protects programming transistor 160 from excessive negative input voltages.

The Q terminal output of the memory shift-register 136 is then applied to the data input of the register extension flip-flop 138 allowing the nth and the (n−1)th memory locations to be sampled simultaneously when n equals the selected delay length. This procedure allows the effective alarm window of one transducer revolution to be increased to allow for wobble in the pipe 24 under test.

The Q output of the register extension flip-flop 138, the memory shift-register 136, and the input latches 134 are then applied to the input of the logical comparator, NAND gate 140. The logical comparator produces an alarm output only when a pulse from an input latch 134 coincides with a pulse from either a memory shift-register 136 or a register extension flip-flop 138.

The outputs of the logical comparators are then applied to the output strobe gate 139. The output strobe gate goes low to alarm condition only when an alarm input from a logical comparator 140 coincides with an output strobe pulse. The purpose of these gates is to block the transitory pulses in the memory shift-register 136 and the register extension flip-flop 138 which occur between the real time and stored time alarm pulses. The output of the strobe gate 139 is then applied to the appropriate output latch (58 in FIG. 3) to the high alarm output system 141.

It will be appreciated that similar circuits 133A and 135A to that provided for the high alarm are provided for each of the alarm circuits here represented as low alarm 133 and flaw alarm 135.

Figure 10:
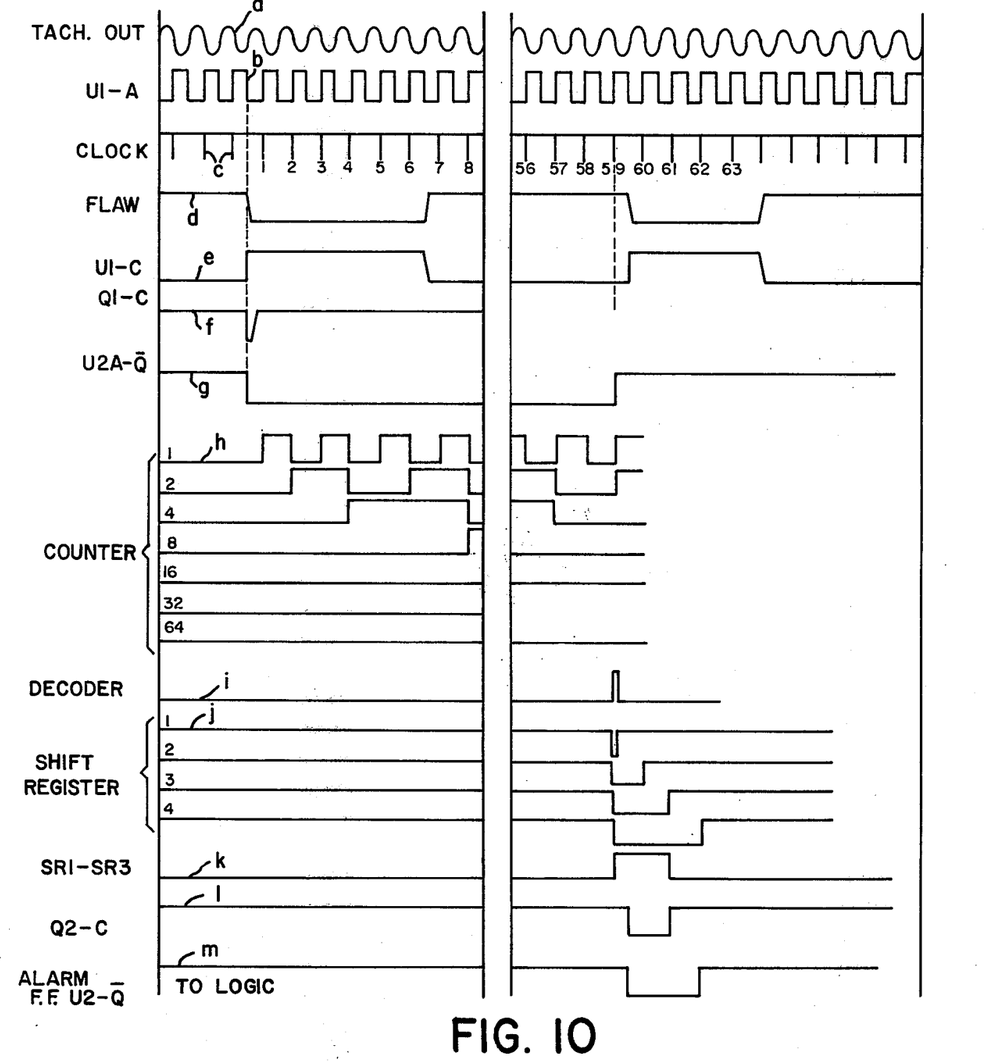
FIG. 10 shows related plots of relevant data with respect to instrumentation of the present invention.

Necessary timing signals, and the like, generated in common for all of the circuits are shown at the top of FIG. 10. In particular, the tachometer input 137 (wave a FIG. 11) is applied to the input of the clock squaring amplifier 142 including transistors 142a and 142b. For purposes of the test, a 60 Hz source 137a can be substituted to the input of the clock squaring amplifier by shorting the terminals which connects a 60 Hz source to the circuit. The clock squaring circuit takes the tachometer wave a of FIG. 10 and produces the square wave b using regenerative means to produce the squared tachometer waveform.

In the absence of a negative input signal, the transistors 142a and 142b are both off. When the input tachometer sine wave goes enough negative transistor 142b turns on transistor 141a and thus forms a regenerative feedback loop. The collector of transistor 142b goes positive, producing the leading edge of the squared tach wave. When the input sine wave goes positive, the regenerative loop reverses causing the collector of the transistor 142b to go negative producing the falling edge of the squared tachometer waveform b. Capacitors C3 and C4 increase the regenerative loop response, thus decreasing the rise and fall times of the squared tachometer waveform b.

The squared tachometer waveform b is differentiated by capacitor C5 and resistor R6 and applied to gate 144 to produce a 10 microsecond output strobe pulse, shown in FIG. 11 as the clock pulse C. The 10 microsecond output strobe pulses are applied to a second differentiator employing transistor 146, capacitor C7, resistors R9 and R10 and gate 148 to produce a 4 microsecond store count pulse.

The 4 microsecond store count clock pulse is inverted by the gate 150 and applied to a third differentiator comprising transistor 152. This differentiator produces the 2 microsecond clear clock pulse at the output of gate 154 which is used to clear and reset the latches 134 in circuits 133A and 135A. Transistor 158, and the corresponding transistors, are drivers for the associated alarm status light-emitting-diode indicators located on the display panel of the equipment. These indicators are held illuminated during all the real time alarm conditions caused by the associated type of fault.

Referring to FIG. 10 so that it may be coordinated with FIG. 9, it will be understood that the signal out of clock squaring amplifier 142 is the line marked b and that the Schmitt trigger generated signal c is the line marked "clock". The diagrams are broken so as not to show the entire count, but a flaw signal d might be recorded somewhat as shown on the chart marked "flaw". The shift-register delay pulses j are shown in lines marked shift-register. SR1 and SR3 represent shift-register signal k which makes it possible to recognize a second flaw signal even when a first flaw signal is being processed by the system. Finally, the last trace m is the output signal at "U2-$\bar{Q}$".

It will occur to those skilled in the art that the specific electronics employed is not the sole means of providing signals for display and alternative means of doing so will occur to those skilled in the art. Details of the display activation circuits have been omitted. However, it may be of interest to indicate in a typical case what happens when the ultrasonic monitor of the present invention has detected a flaw or has found the out of tolerance and, therefore, activated the alarm circuit. First, a horn sounds, alerting the operator, and a light goes on overhead indicating which production line is affected. A red light on the monitoring panel board also indicates which alarm circuit (low wall, high wall, and/or rate-of-change) has been activated. The alarm period can be adjusted between 0.2 to 5 seconds, at which time a green "accept" light comes on. The "accept" light stays on so long as the pipe stays within the alarm limits. The alarms can also be placed in a latched condition. The latched condition requires that a green "accept" button must be pushed to deactivate the horn and lights.

If the pipe stays outside of alarm limits for an extended period of time, as happens during startup, a "silent" button can be depressed to disable the horn, only. All other alarm functions remain operative.

An event marker on the wall thickness recorder will also react to a flaw and further provide a permanent record of a flaw condition.

Finally, the Scanner can be provided with a paint sprayer that marks the pipe to assist in locating the defect. During startups, the paint sprayer is bypassed by the silent button.

And finally, various modifications to the present invention will occur to those skilled in the art. It will be clear that modifications will be required for different sizes of pipe and equipment will differ depending upon how monitoring is actually carried out. One of the big factors always being the size of a pipe. Size capability for the prototype was ½ inch through 2 inch pipe. However, in order to provide inspection for all standard DuPont Aldyl® pipe sizes, a second machine with capability to inspect 2 inches through 6 inches was provided. It will be observed that the two sizes overlapped a 2 inch pipe which is perhaps a most popular production size. It is anticipated, however, that as pipe sizes are increased, the present invention will be capable of being adapted to handle the increased pipe size.

Other modifications within the scope of the claims will occur to those skilled in the art. All such modifications are intended to be within the scope and spirit of the present invention.

We claim:

1. A system for inspecting the wall of tubular material in which the tubular material passes through an inspection apparatus including a chamber supplied with fluid to fill the path between the tubular material and ultrasonic transducer means providing means to transmit ultrasonic pulses inwardly to the tubular material and receive pulses reflected at least from the outer and inner wall surfaces of said tubular material and means to provide relative rotation of the ultrasonic transducer means around the tubular material as said tubular material passes generally axially through said chamber, comprising:

a pulse generating source for the ultrasonic transducer means to provide pulses at a constant rate sufficiently frequent to permit examination of the entire tubular material;

a pulse receiving and interpreting means for effectively calculating wall thickness of the tubular material opposite a transducer location;

an out-of-tolerance comparison means to identify out-of-tolerance data in comparison to a predetermined in-tolerance standard, a storage means to receive and store an out-of-tolerance output signal from the comparison means in a position representative of sensor and tubular location;

angular location means secured relative to said ultrasonic transducer means for rotation therewith, said angular location means having a repetitive pattern providing preselected number of pattern repetitions around its periphery;

stationary sensor means cooperating with the repetitive pattern on the angular location means to produce a repetitive wave-form output representative of transducer location;

means responsive to each wave of said repetitive wave-form output to count waves and thereby provide a basis for comparison of a stored out-of-tolerance signal at a predetermined position relative to the currently generated signal;

means for comparing said stored output signal with the output existing at the attainment of a preselected count of a number of waves from a counter corresponding to a comparison position for verification, and producing a verification signal upon comparison if the signals correspond within preset limits, and out-of-tolerance indicator means receiving said verification of said out-of-tolerance signal from the comparison means and indicating the out-of-tolerance condition.

2. The system of claim 1 in which the counter counts for the equivalent of a complete revolution, or a predetermined limited number of counts before or after a full revolution, before making comparison.

3. The system of claim 1 in which the storage means is a shift register in which data is periodically shifted by the signals from the stationary sensor means and comparison is made at a predetermined comparison position for verification approximately one revolution later.

4. The system of claim 3 in which the angular location means is a toothed wheel.

5. The system of claim 4 in which the number of teeth on said wheel is 60 and said preselected number of waves is 60.

6. The system of claim 4 in which the number of teeth on said wheel is 60 and said preselected number of waves is 59.

7. The system of claim 4 in which the said constant rate of said pulse generating source is about 3,000 cycles per second.

8. A system for inspecting tubular material in which the tubular material passes through an inspection apparatus including a chamber supplied with liquid to fill the path between the tubular material and ultrasonic transducer means providing means to transmit ultrasonic pulses inwardly to the tubular material and receive pulses reflected at least from the outer and inner wall surfaces of said tubular material and means to provide relative rotation of the ultrasonic transducer means around the tubular material as said tubular material passes generally axially through said chamber, comprising:

a pulse generating source for the ultrasonic transducer means to provide pulses at a rate sufficiently frequent to permit examination of the entire tubular material;

a pulse receiving and interpreting means for generating a signal representative of rate-of-change of wall thickness of the tubular material at successive measurement intervals around the tube;

comparison means for comparing the dimensional wall thickness rate-of-change signals with at least one predetermined rate-of-change tolerance limit to identify flaws; and out-of-tolerance indicator means receiving an output signal from the comparison means indicating a flaw.

9. The system of claim 8 in which a high pass filter is used to identify a flaw signal from passed high frequencies generated by a preselected rate-of-change of tubular wall thickness.

10. The system of claim 8 in which a plurality of tuned band pass filters are used in parallel to identify an array of flaw signals from passed high frequencies generated by a preselected rate-of-change of tubular wall thickness.

11. The system of claim 8 in which the comparison means includes a peak detector employed in obtaining maximum wall thickness signals and a storage device is provided to receive and hold at least previous maximum peak readings.

12. The system of claim 11 in which two stages of operational amplifiers are used with storage means between them and the second amplifier is used as a high impedance voltage-follower.

13. The system of claim 12 in which the first operational amplifier is used as a diode detector to permit precision rectification of small signals.

14. The system of claim 13 in which the second operational amplifier in combination with a diode and at least two resistors to produce a constant current discharge for the storage means.

15. The system of claim 14 in which a rate-of-change filter is employed at circuit output.

16. The system of claim 15 employs a peak detector at output for maximum wall thickness detection.

17. The system of claim 15 employs a peak detector at output for minimum wall thickness detection.

18. The system of claim 8 in which the comparison means includes a peak detector employed in obtaining minimum wall thickness signals and the storage device is provided to receive and hold at least minimum peak readings.

19. The system of claim 18 in which two stages of operational amplifiers are used with storage means between them and the second amplifier is used as a high impedance voltage-follower.

20. The system of claim 19 in which the first operational amplifier is used as a diode detector to permit precision rectification of small signals.

21. The system of claim 20 in which the second operational amplifier in combination with a diode and at least two resistors to produce a constant current discharge for the storage means.

* * * * *